United States Patent
Liao et al.

(10) Patent No.: US 11,076,040 B2
(45) Date of Patent: Jul. 27, 2021

(54) WIRELESS COMMUNICATION DEVICE AND SUBSCRIBER IDENTITY MODULE CARD IN THE WIRELESS COMMUNICATION DEVICE

(71) Applicant: AI Nose Corporation, New Taipei (TW)

(72) Inventors: Yu-Hsuan Liao, Miaoli County (TW); Chia-Pin Huang, Miaoli County (TW); Chun-Hsien Tsai, Miaoli County (TW); Ting-Chuan Lee, Miaoli County (TW); Chun-Jung Tsai, Miaoli County (TW)

(73) Assignee: AI NOSE CORPORATION, New Taipei (TW)

( * ) Notice: Subject to any disclaimer, the term of this patent is extended or adjusted under 35 U.S.C. 154(b) by 0 days.

(21) Appl. No.: 16/871,871

(22) Filed: May 11, 2020

(65) Prior Publication Data
US 2020/0366782 A1 Nov. 19, 2020

(30) Foreign Application Priority Data

May 15, 2019 (TW) .................................. 108116768

(51) Int. Cl.
*H04B 1/38* (2015.01)
*H04M 1/72454* (2021.01)
(Continued)

(52) U.S. Cl.
CPC .... *H04M 1/72454* (2021.01); *G01N 33/0027* (2013.01); *H04B 1/3816* (2013.01); *H04B 2001/3894* (2013.01); *H04M 2250/12* (2013.01)

(58) Field of Classification Search
CPC .. H04M 1/23; H04M 1/0249; H04M 1/72454; H04B 1/3816
See application file for complete search history.

(56) References Cited

U.S. PATENT DOCUMENTS 9,141,905 B2 * 9/2015 Baek ................ G06K 19/07771
10,310,562 B2 * 6/2019 Choi ..................... G06F 1/1656
(Continued)

FOREIGN PATENT DOCUMENTS

| CN | 208283368 U | 12/2018 |
| TW | 201332515 A1 | 8/2013 |

*Primary Examiner* — Tuan Pham
(74) *Attorney, Agent, or Firm* — Muncy, Geissler, Olds & Lowe, P.C.

(57) ABSTRACT

The present invention provides a wireless communication device and a subscriber identity module card in a wireless communication device. The subscriber identity module card comprises a flat plate carrier, a subscriber identity module circuit and a gas sensing chip. The flat plate carrier comprises a first surface where the subscriber identity module circuit is disposed, a second surface where the gas sensing chip is disposed, a through hole, and an electrical contact portion passing through the through hole and extending to reach the first surface and the second surface. The electrical contact portion is electrically connected to the subscriber identity module circuit and the gas sensing chip. The gas sensing chip is disposed on a portion of the subscriber identity module card where not occupied by the subscriber identity module circuit. Thus, the wireless communication device provides gas sensing function without additionally equipping with an external gas sensing element.

8 Claims, 5 Drawing Sheets

(51) Int. Cl.
 *G01N 33/00* (2006.01)
 *H04B 1/3816* (2015.01)

(56) References Cited

U.S. PATENT DOCUMENTS

2004/0129890 A1* 7/2004 Berman .................. G01T 1/178
                                                  250/380
2019/0120805 A1* 4/2019 Kwak ................... G01N 1/2273
2019/0265082 A1* 8/2019 Zafar ....................... G01D 7/00

* cited by examiner

WIRELESS COMMUNICATION DEVICE AND SUBSCRIBER IDENTITY MODULE CARD IN THE WIRELESS COMMUNICATION DEVICE

FIELD OF THE INVENTION

The present invention relates to a wireless communication device and a subscriber identity module card in the wireless communication device, and more particularly to a subscriber identity module card with gas sensing function and a subscriber identity module card in a wireless communication device with the SIM card.

BACKGROUND OF THE INVENTION

Gas sensors are widely used to sense the physical properties or chemical properties of gases, and are popularly applied in medical, industrial and environmental protection fields. For example, the Taiwan publication number 1458464 mentions a respirator that can detect and identify the type of pneumonia at an early stage.

Further, a gas sensor of a handheld device is provided in the Chinese utility model publication number CN 208283368 U. The gas sensor includes a sensing chip, a circuit board, and a gas passage and is installed in a cavity of the handheld device that accommodates a microphone. The handheld device is a portable information device such as mobile phone, tablet computer, personal digital assistant (PDA), etc. Therefore, users can use the handheld device to perform air (gas) sensing function at any time to maintain personal health or ensure work safety. Besides, it is easy to adopt appropriate countermeasures for severe air pollution problems by observing the value of fine suspended particulates (PM2.5) in the air at any time.

However, installation space and circuit contacts in the cavity must be available for installing the gas sensor in the cavity of the handheld device disposed with the microphone. Nowadays, as handheld devices tend to become thinner than ever, installation space and circuit contacts should be reserved in the design procedure of the handheld device to install the gas sensor. Thus, it is difficult to install the gas sensor if installation space and circuit contacts are not reserved before the design procedure, causing handheld devices only can be maintained and replaced by expertise of disassembling the handheld device.

In addition, users are not willing to install the gas sensor since the user will lose the warranty of the handheld device by dissembling the handheld device to install the gas sensor in the cavity of the microphone.

SUMMARY OF THE INVENTION

A main object of the present invention is to solve the problem that conventional wireless communication devices with gas sensing function need to be additionally equipped with a gas sensor externally.

A secondary object of the present invention is to provide a subscriber identity module card modularized to be disassembled and replaced by users according to the type of a wireless communication device, so that the wireless communication device has the function of a gas sensor.

In order to achieve the above objects, the present invention provides a wireless communication device comprising a body, a plug-in unit and a subscriber identity module card. The body comprises a casing, a board, an opening and a slot, the board is disposed inside the casing, the opening is disposed on the casing, and the slot is connected with the opening. The plug-in unit comprises a frame, an outer cover, and a permeable waterproof membrane. The frame is inserted into the slot, and the outer cover is plugged in the opening. The permeable waterproof membrane is located between the frame and the outer cover for sealing the opening to allow gas to pass through but block water out. The outer cover comprises at least one gas through hole capable of allowing a space in the slot to communicate externally through the at least one gas through hole, and allowing gas to enter the slot.

The subscriber identity module card comprises a flat plate carrier, a subscriber identity module circuit and a gas sensing chip. The flat plate carrier is mounted on the frame, and when the frame is inserted into the slot, the subscriber identity module circuit is electrically connected to the board. The flat plate carrier comprises a first surface, a second surface, a through hole, and an electrical contact portion. The first surface is disposed on the subscriber identity module circuit; the second surface is opposite to the first surface and is disposed on the gas sensing chip. The through hole penetrates the first surface and the second surface, the electrical contact portion passes through the through hole and extends to reach the first surface and the second surface, and the electrical contact portion is electrically connected to the subscriber identity module circuit and the gas sensing chip.

Compared with the prior art, the gas sensing chip of the present invention is disposed on a portion of the subscriber identity module where not occupied by the subscriber identity module circuit, and comprises the permeable waterproof membrane and the gas through hole. Thus, the wireless communication device provides gas sensing function without additionally equipped with an external gas sensing element. Besides, the permeable waterproof membrane allows gas to enter into the wireless communication device but block water out so as to meet the requirements of waterproof and gas sensing. Further, the subscriber identity module card and the gas sensing chip are modularized and integrally designed, and the original standard interface of the subscriber identity module card is installed on the wireless communication device without changing the hardware of the wireless communication device, which is applicable to various types and models of wireless communication devices and thereby users can replace the subscriber identity module card by themselves to meet the needs of usage and self-maintenance.

DETAILED DESCRIPTION OF THE PREFERRED EMBODIMENTS

The detailed description and technical contents of the present invention are described below with reference to the drawings.

Figure 1:
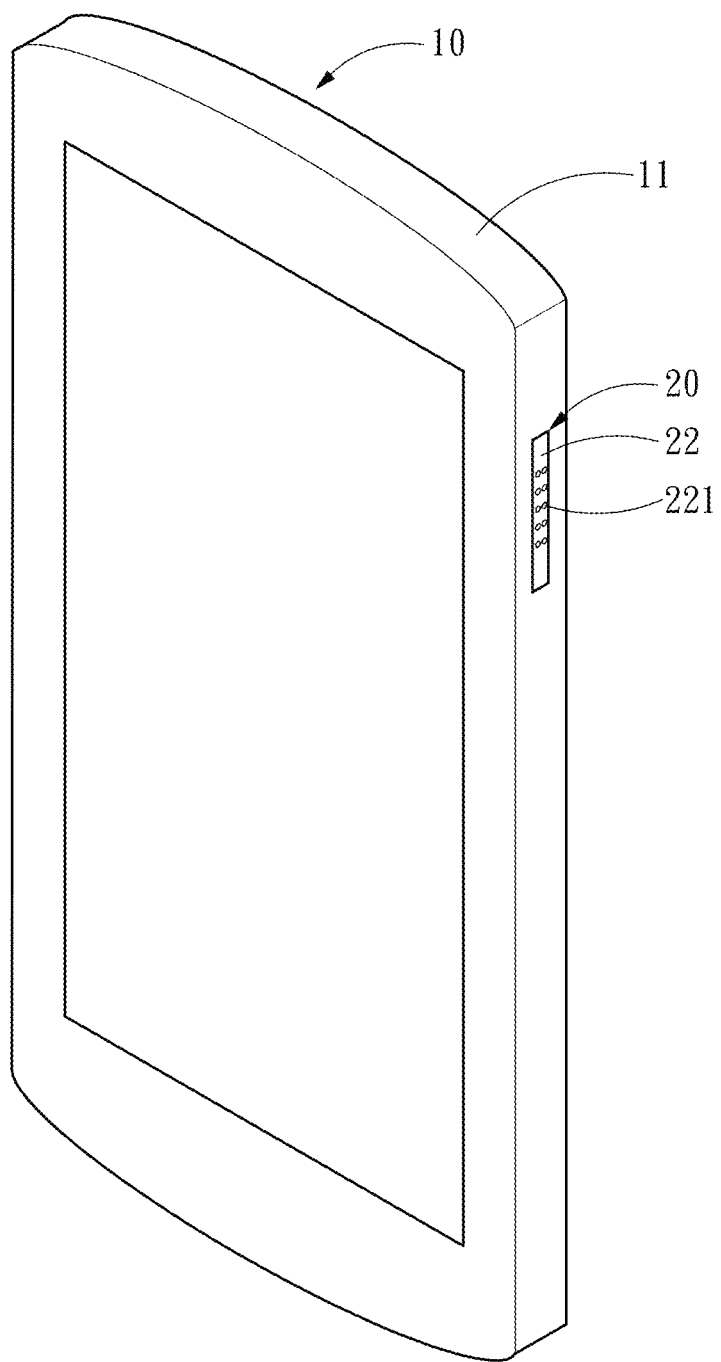
FIG. 1 is a perspective view of an assembly structure of a first embodiment of the present invention.
Figure 2:
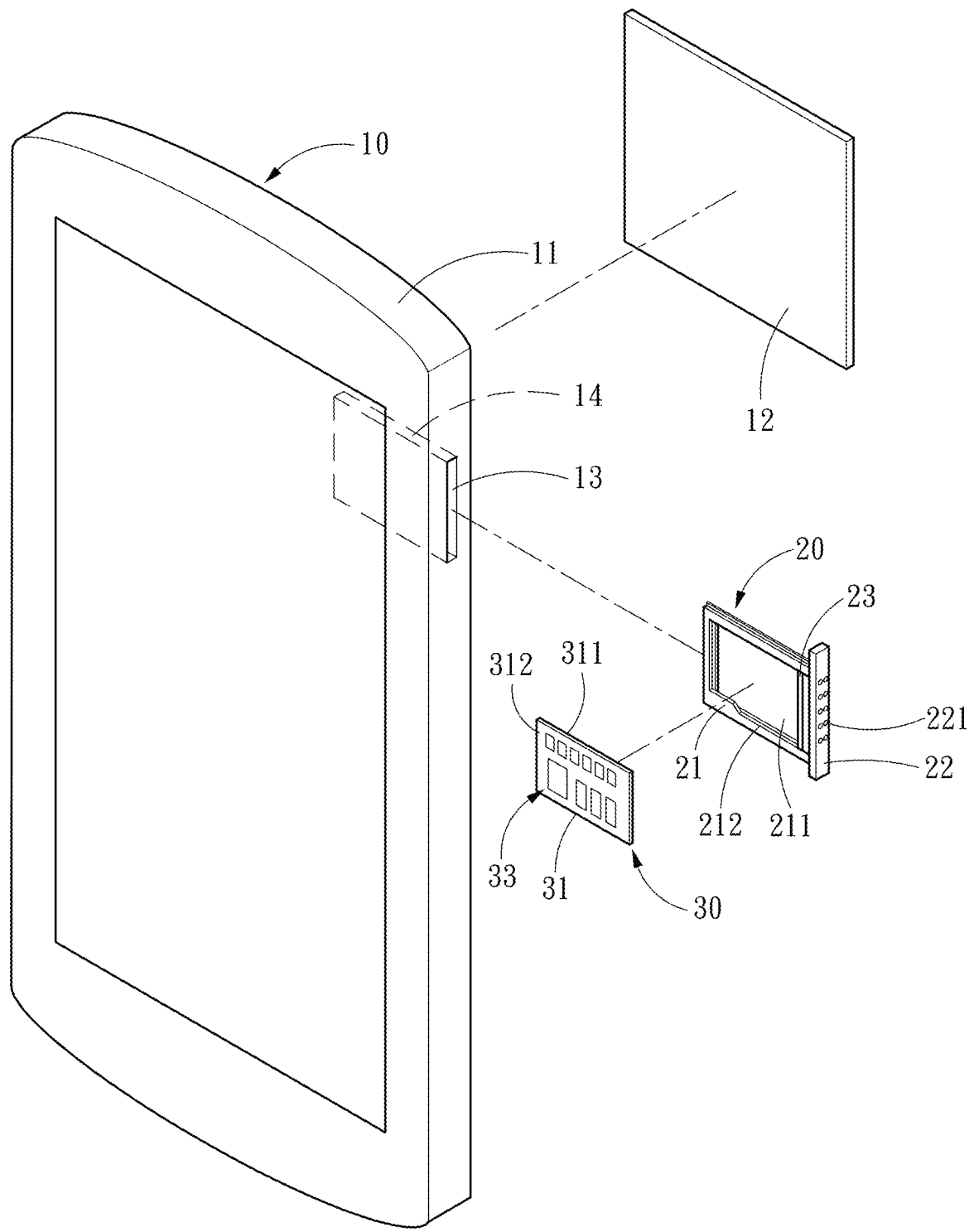
FIG. 2 is an exploded perspective structural view of the first embodiment of the present invention.
Figure 3:
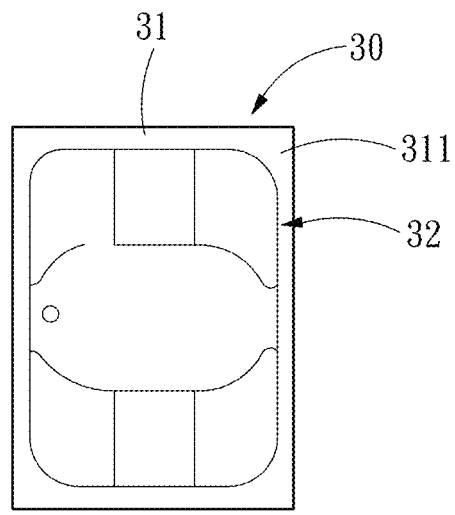
FIG. 3 is a schematic structural diagram of a backside of a subscriber identity module card of the first embodiment of the present invention.

Please refer to FIG. 1, FIG. 2, and FIG. 3. The present invention provides a wireless communication device including a body 10, a plug-in unit 20 and a subscriber identity module card 30. The body 10 includes a casing 11, a board 12, an opening 13, and a slot 14. The board 12 is disposed inside the casing 11, the opening 13 is disposed on the casing 11, and the slot 14 is connected with the opening 13. In one embodiment, the wireless communication device is a mobile phone. In other embodiments, the wireless communication device is a tablet computer or other similar devices or devices with the same functions.

The plug-in unit 20 comprises a frame 21, an outer cover 22, and a permeable waterproof membrane 23. The frame 21 is inserted into the slot 14, and the outer cover 22 is plugged in the opening 13. The permeable waterproof membrane 23 is located between the frame 21 and the outer cover 22 for sealing the opening to allow gas to pass through but block water out. The outer cover 22 comprises at least one gas through hole 221, and a space in the slot 14 communicates externally through the at least one gas through hole 221, so that gas pass through and enter the slot 14.

A size of the subscriber identity module card 30 is compatible with the traditional subscriber identity module (SIM) cards, such as full-size SIM card, mini-SIM card, micro-SIM card, or nano-SIM card. The subscriber identity module card 30 comprises a flat plate carrier 31, a subscriber identity module circuit 32, and a gas sensing chip 33. The flat plate carrier 31 is mounted on the frame 21 to fix the subscriber identity module card 30 on the frame 21. The frame 21 comprises at least one open slot 211 surrounded by a rim 212, and the flat plate carrier 31 is located against on the rim 212. After the frame 21 is inserted into the slot 14, the subscriber identity module circuit 32 is electrically connected to the board 12.

Figure 4:
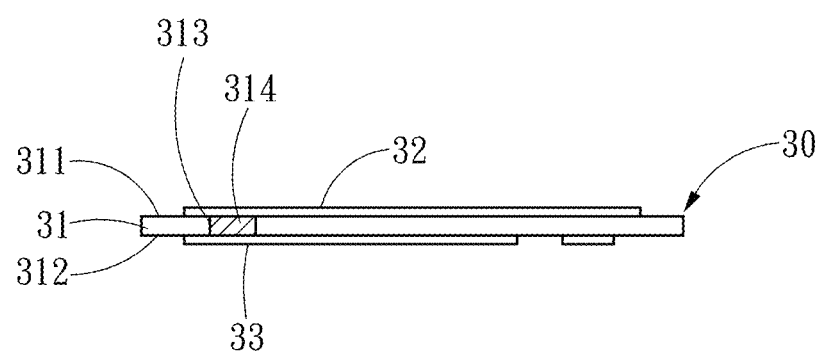
FIG. 4 is a cross-sectional structural view of the subscriber identity module card of the first embodiment of the present invention.
Figure 5:
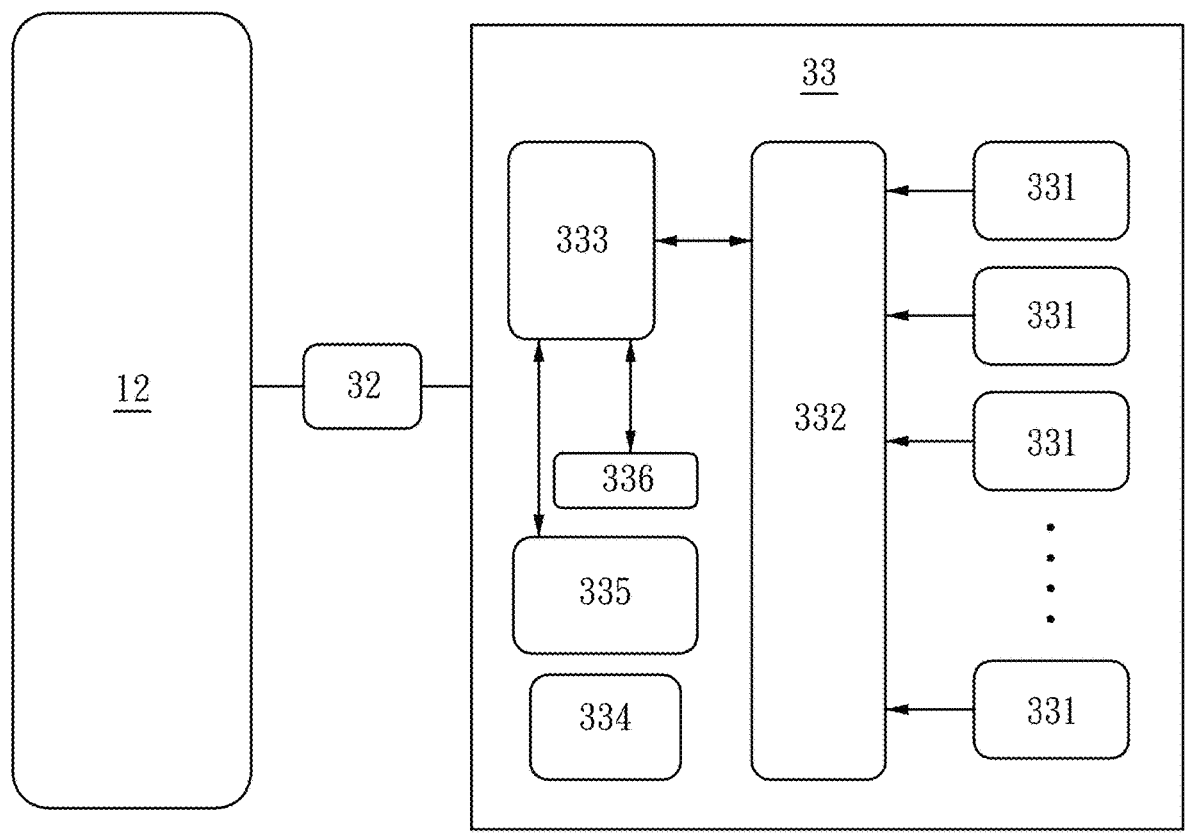
FIG. 5 is a block diagram of a system architecture of the first embodiment of the present invention.

Please refer to FIG. 4. The flat plate carrier 31 comprises a first surface 311, a second surface 312, a through hole 313, and an electrical contact portion 314. The first surface 311 is provided with the subscriber identity module circuit 32. The subscriber identity module circuit 32 is the same as a circuit structure of a subscriber identity module card, and is composed of CPU, ROM, RAM, EEPROM, and I/O circuits. The composition of the subscriber identity module circuit 32 is well known and understood in the art, and thus is not described in great detail here. The second surface 312 is opposite to the first surface 311 and the gas sensing chip 33 is disposed on the second surface 312. The through hole 313 penetrates the first surface 311 and the second surface 312, and the electrical contact portion 314 passes through the through hole 313 and extends to reach the first surface 311 and the second surface 312, and the electrical contact portion 314 is electrically connected to the subscriber identity module circuit 32 and the gas sensing chip 33. In this way, since the subscriber identity module circuit 32 is electrically connected to the board 12 as shown in FIG. 5, the gas sensing chip 33 is indirectly electrically connected to the board 12 via the subscriber identity module circuit 32 while the gas sensing chip 33 is electrically connected to the subscriber identity module circuit 32 via the electrical contact portion 314. Thus, the board 12 provides a required voltage to the gas sensing chip 33, and the board 12 is used as an input/output interface.

Please refer to FIG. 5. The gas sensing chip 33 comprises at least one gas sensing element 331, an analog-digital conversion unit 332, a micro processing unit 333, a power management unit 334, a data storage unit 335, and a temperature and humidity sensor 336. The analog-digital conversion unit 332 is connected to the at least one gas sensing element 331, and the at least one gas sensing element 331 is selected from a sensor involving in micro-electromechanical system (MEMS), electrochemistry, high polymer and optics. The micro processing unit 333 is connected to the analog-digital conversion unit 332. The analog-digital conversion unit 332 converts analog signals sensed by the at least one gas sensing element 331 into digital signals, and the power management unit 334 is connected to the electrical contact portion 314 (please refer to FIG. 4) and supplies the required voltage to the gas sensing chip 33. The data storage unit 335 is connected to the micro processing unit 333, and the data storage unit 335 is selected from a flash memory, an electrically-erasable programmable read-only memory (EEPROM), etc., for temporarily storing digital data. The temperature and humidity sensor 336 is also connected to the micro processing unit 333, and is used for sensing temperature and humidity.

Figure 6:
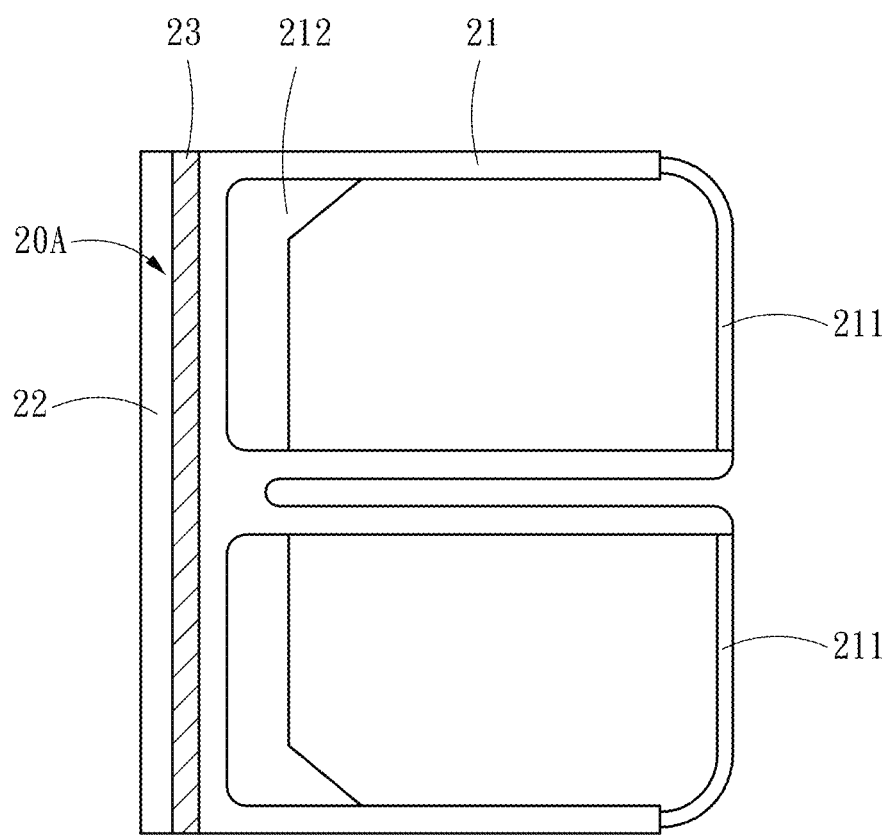
FIG. 6 is a schematic structural diagram of a plug-in unit of a second embodiment of the present invention.

Please refer to FIG. 6. A quantity of the open slot 211 of the plug-in unit 20A is two, provided for installing two subscriber identity module cards 30, that is, the invention comprises at least one open slot 211 based on the specifications of the wireless communication device. Further, the size of the open slot 211 corresponds to the specifications of the subscriber identity module card 30.

In summary, the present invention provides the wireless communication device and the subscriber identity module card with built-in gas sensing function. Compared with the conventional techniques, the present invention has the following features:

1. The gas sensing chip of the present invention is disposed on a portion of the subscriber identity module where not occupied by the subscriber identity module circuit, and comprises the permeable waterproof membrane and the gas through hole. Thus, the wireless communication device provides gas sensing function without additionally equipped with an external gas sensing element.

2. The subscriber identity module card and the gas sensing chip are modularized and integrally designed based on the wireless communication device to be installed, and thereby the function of the gas sensing chip is applied to the wireless communication device without changing the hardware of the wireless communication device.

3. The original standard interface of the subscriber identity module card is applied to various types and models of wireless communication devices, and users can replace the subscriber identity module card to meet the needs of usage and self-maintenance.

4. The permeable waterproof membrane and the gas through hole provides the function of blocking water to meet the requirements of waterproof and gas sensing under the condition allowing gas to pass through.

5. The subscriber identity module circuit and the gas sensing chip are electrically connected through the electrical contact portion that passes through the through hole and extends to reach the first surface and the second surface. Therefore, the gas sensing chip is electrically connected to the board of the wireless communication device through the subscriber identity module circuit, and then the board provides a required voltage to the gas sensing chip and serves as a communication interface.

What is claimed is:

1. A wireless communication device including:
   a body, the body comprising a casing, a board disposed inside the casing, an opening disposed on the casing, and a slot connected with the opening;
   a plug-in unit, the plug-in unit comprising a frame inserted into the slot, an outer cover plugged in the opening, and a permeable waterproof membrane located between the frame and the outer cover for sealing the opening, the outer cover comprising at least one gas through hole; and
   a subscriber identity module card, the subscriber identity module card comprising a flat plate carrier mounted on the frame, a subscriber identity module circuit electrically connected to the board, and a gas sensing chip, the flat plate carrier comprising a first surface on which the subscriber identity module circuit is disposed, a second surface opposite to the first surface and on which the gas sensing chip is disposed, a through hole penetrating the first surface and the second surface, and an electrical contact portion passing through the through hole and extending to reach the first surface and the second surface, and the electrical contact portion electrically connected to the subscriber identity module circuit and the gas sensing chip.

2. The wireless communication device as claimed in claim 1, wherein the frame comprises at least one open slot, and the at least one open slot comprises a rim against the flat plate carrier.

3. The wireless communication device as claimed in claim 1, wherein the gas sensing chip comprises at least one gas sensing element, an analog-digital conversion unit connected to the at least one gas sensing element, a micro processing unit connected to the analog-digital conversion unit, and a power management unit connected to the electrical contact portion and supplying a required voltage to the gas sensing chip.

4. The wireless communication device as claimed in claim 3, wherein the gas sensing chip further comprises a data storage unit connected to the micro processing unit, and a temperature and humidity sensor connected to the micro processing unit.

5. A subscriber identity module card including:
   a flat plate carrier, the flat plate carrier comprising a first surface, a second surface opposite to the first surface, a through hole penetrating the first surface and the second surface, and an electrical contact portion passing through the through hole and extending to reach the first surface and the second surface;
   a subscriber identity module circuit, the subscriber identity module circuit disposed on the first surface, and the subscriber identity module circuit electrically connected to the electrical contact portion; and
   a gas sensing chip, the gas sensing chip disposed on the second surface, and the gas sensing chip electrically connected to the electrical contact portion.

6. The subscriber identity module card as claimed in claim 5, wherein the subscriber identity module card further comprising a plug-in unit, the plug-in unit comprising a frame, an outer cover, and a permeable waterproof membrane located between the frame and the outer cover, the outer cover comprising at least one gas through hole, the frame comprising at least one open slot, and the at least one open slot comprising a rim against the flat plate carrier.

7. The subscriber identity module card as claimed in claim 5, wherein the gas sensing chip comprises at least one gas sensing element, an analog-digital conversion unit connected to the at least one gas sensing element, a micro processing unit connected to the analog-digital conversion unit, and a power management unit connected to the electrical contact portion and supplying a required voltage to the gas sensing chip.

8. The subscriber identity module card as claimed in claim 7, wherein the gas sensing chip further comprises a data storage unit connected to the micro processing unit, and a temperature and humidity sensor connected to the micro processing unit.

* * * * *